(12) United States Patent
Schubart et al.

(10) Patent No.: US 6,506,178 B1
(45) Date of Patent: Jan. 14, 2003

(54) APPARATUS AND METHOD FOR CROSSING A POSITION ALONG A TUBULAR BODY STRUCTURE

(75) Inventors: Peter J. Schubart, Los Altos Hills, CA (US); Ted S. Thorson, Sunnyvale, CA (US); John D. Martin, Potomac, MD (US)

(73) Assignee: Vascular Architects, Inc., San Jose, CA (US)

( * ) Notice: Subject to any disclaimer, the term of this patent is extended or adjusted under 35 U.S.C. 154(b) by 152 days.

(21) Appl. No.: 09/709,762

(22) Filed: Nov. 10, 2000

(51) Int. Cl.[7] .............................................. A61M 11/00
(52) U.S. Cl. ................................... 604/93.01; 606/159
(58) Field of Search ...................... 604/93.01, 103.03, 604/528, 467, 164.01, 95.01; 600/585, 407; 606/159, 148; 623/1.11

(56) References Cited

U.S. PATENT DOCUMENTS

| | | | |
|---|---|---|---|
| 4,774,949 A | 10/1988 | Fogarty | |
| 5,385,152 A * | 1/1995 | Abele et al. ................. | 600/585 |
| 5,624,396 A * | 4/1997 | McNamara et al. ...... | 604/93.01 |
| 5,741,270 A | 4/1998 | Hansen et al. | |
| 5,820,629 A * | 10/1998 | Cox ............................ | 606/159 |
| 5,968,064 A | 10/1999 | Selmon et al. | |
| 6,090,135 A * | 7/2000 | Plaia et al. .................. | 623/1.11 |
| 6,117,145 A * | 9/2000 | Wood et al. ................. | 606/148 |
| 6,190,353 B1 * | 2/2001 | Makower et al. ......... | 604/95.01 |
| 6,235,000 B1 * | 5/2001 | Milo et al. ............... | 604/164.01 |
| 6,241,667 B1 * | 6/2001 | Vetter et al. ................ | 600/407 |
| 6,241,745 B1 * | 6/2001 | Rosenthal ................... | 606/159 |
| 6,302,875 B1 * | 10/2001 | Makower et al. ........... | 604/528 |
| 6,309,379 B1 * | 10/2001 | Willard et al. .............. | 604/467 |
| 6,312,407 B1 * | 11/2001 | Zadno-Azizi et al. .. | 604/103.03 |
| 2002/0029052 A1 * | 3/2002 | Evans et al. ................ | 606/159 |

FOREIGN PATENT DOCUMENTS

| WO | WO 00/18323 A3 | 4/2000 |
|---|---|---|
| WO | WO 00/18323 A2 | 4/2000 |

OTHER PUBLICATIONS

Bernhard Meier, "Chronic Total Occlusion," Textbook of Interventional Cardiology, 1994, Chapter 16, pp. 318–338, vol. 1, Second Edition, W. B. Saunders Company.

Bernhard Meier, "Chronic Total Occlusion," Textbook of Interventional Cardiology, Chapter 15, pp. 280–296, Third Edition, W. B. Saunders Company.

Mark Freed, M.D., "Chronic Total Occlusion," Manual of Interventional Cardiology, pp. 293–320.

Jaap N. Hamburger and Patrick W. Serruys, "Laser guidewire for recanalizatio of chronic total occlusions," Frontiers in Interventional Cardiology, 1997, pp. 47–53, Martin Dunitz Ltd., United Kingdom.

Bernhard Meier, "Total Occlusion," Practical Angioplasty, 1994, Chapter 10, pp. 101–119, Raven Press, Ltd., United States of America.

"Cardiovascular Disease, Current Treatment Options and Chronic Total Occlusions," http://www.lumend.com.

M. Selmon, et al., "Blunt Controlled Micro–Dissection for Percutaneous Revascularization of Chronic Total Occlusions in Peripheral Arteries," http://www.lumend.com/cto_abstracts_acc99.html.

"LuMend Introduces New Option For Treating Chronic Total Occlusions," Abstract Presented at American College of Cardiology's 48th Annual Scientific Session, http://www.lumend.com/about_news_3_8_99.html.

"LuMend, Inc. Introduces New Products For Treatment of Chronic Total Occlusions,"—Dr. Peter Mossop Joins Panel of International Experts at Endovascular Therapy Course—, http://www.lumend.com/about_news_5_19 _9.html.

* cited by examiner

Primary Examiner—Teresa Walberg
Assistant Examiner—Leonid Fastovsky
(74) Attorney, Agent, or Firm—James F. Hann; Haynes Beffel & Wolfeld LLP

(57) ABSTRACT

A vascular occlusion-crossing assembly (2) includes an elongate delivery system (4) and a flexible elongate member (6) which passes along the body (34) of the delivery assembly. A laterally-extending, vascular tunica-separation guide (32) helps guide the distal end (36) of the delivery assembly between tunica layers (40, 42, 44) to a position distal of an occlusion (52). The distal portion (30) of a distally moving elongate member, typically a flexible hollow needle, is deflected into this distal lumen (54) on the far side of an occlusion (52). A guidewire (62) may be passed along the elongate member thereby crossing the occlusion.

68 Claims, 8 Drawing Sheets

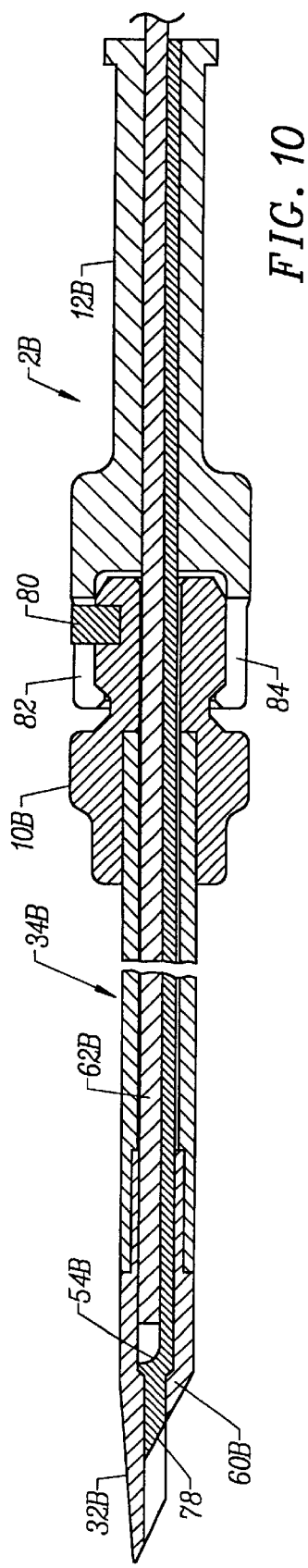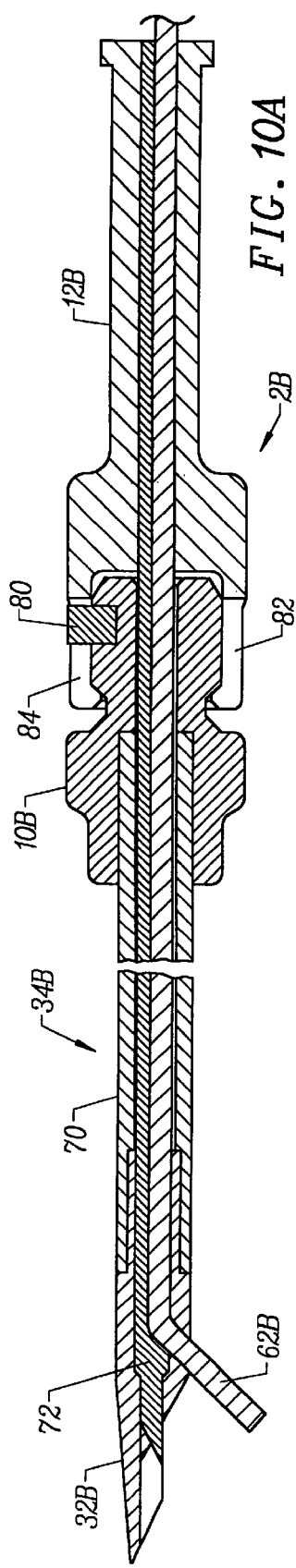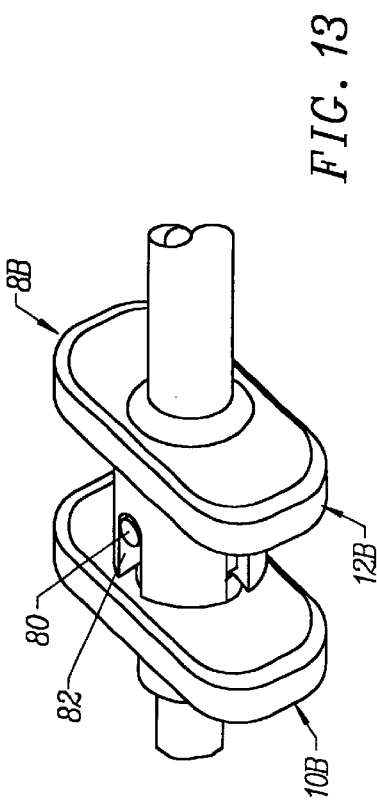

APPARATUS AND METHOD FOR CROSSING A POSITION ALONG A TUBULAR BODY STRUCTURE

CROSS-REFERENCES TO RELATED APPLICATIONS

None.

STATEMENT AS TO RIGHTS TO INVENTIONS MADE UNDER FEDERALLY SPONSORED RESEARCH AND DEVELOPMENT

None.

BACKGROUND OF THE INVENTION

Remote endarterectomy is a procedure by which a single incision is made at one position along a blood vessel to provide access to the blood vessel by some type of ring stripper. The remote endarterectomy procedure is often accomplished when the blood vessel is totally occluded. The ring stripper, which typically consists of a ring at the end of a long thin handle, is typically passed between the tunica intima (also called the intimal layer) and the tunica media under fluoroscopic guidance thus dissecting the intimal layer and the occlusion from the remainder of the vessel wall to a position distal of the occlusion. The ring stripper is then removed and a remote cutter, such as described in U.S. Pat. No. 5,843,102, can be used to transect the separated intimal layer distally of the occlusion. This permits the intimal layer and the occlusion to be removed through the single incision proximal of the occlusion.

One of the problems with conventional remote endarterectomy procedures occurs because removing the intimal layer and obstruction tends to pull sections of the intimal layer away from the remainder of the vessel wall at the point of transection. This leaves flaps of the transected intimal layer partially obstructing the lumen of the vessel. The intimal layer flaps interfere with the passage of a guidewire to a position distal of the transected intimal layer. Guidewires are used for many purposes, such as to guide passage of a balloon, stent or other endoluminal prosthesis into position to secure the intimal layer flaps outwardly against the remainder of the vessel wall. However, the obstruction caused by the intimal layer flaps tends to deflect the guidewire into the natural dissection plane between the tunica intima and the tunica media. Guidewire placement can occasionally be a tedious and time consuming procedure for the surgeon. If the guidewire enters this natural dissection plane, it may travel distally along the plane, giving the surgeon are impression that the true lumen has been accessed when in fact the surgeon has created a false lumen. This can also create damage to the vessel, forcing conversion to conventional bypass surgery. If it is not possible to pass the guidewire past the intimal lining flaps, the surgeon may be forced to make a separate incision past the transected intimal layer and use this second opening into the vessel to permit the guidewire to be passed retrograde through the second incision, through the vessel and out through the first incision. At times it may be required that the vessel be opened up surgically at the end point and treat the intimal lining flap surgically. Both of these latter two options largely negate the advantages of the remote endarterectomy procedure.

PCT publication WO 00/18323 discloses apparatus for guiding a guidewire between the intimal and adventitial layers of a blood vessel wall, past an occlusion and back into the main lumen distal of the occlusion. The device, however, lacks structure which would help maintain the end of the catheter body between the intimal and adventitial layers. It also lacks structure which would limit the distance the guidewire could extend through the device and into the blood vessel. In addition to lacking any recognition of the desirability of such structure, the reference fails to recognize the desirability for the use of a contrast medium to ensure the guidewire has properly accessed the distal lumen.

SUMMARY OF THE INVENTION

The present invention provides an assembly and method by which a guidewire can be positioned across a vascular occlusion prior to removal of the occlusion. This eliminates the problems associated with guidewire placement following removal of a total occlusion by a remote endarterectomy procedure. The invention is not limited to endarterectomy procedures nor is it limited to blood vessels. The invention may be used with vascular structures, including arteries and veins in various locations such as iliac, SFA, renal, coronary, SV bypass grafts and the like, as well as non-vascular tubular body structures, such as bile ducts and the esophagus. The invention may be used to cross total or partial occlusions or to cross an unoccluded position along a hollow body structure. However, for ease of discussion, the invention will usually be discussed in terms of crossing a total vascular occlusion in conjunction with a remote endarterectomy procedure.

A first aspect of the invention is directed to an assembly comprising an elongate member delivery assembly and a flexible elongate member, typically a hollow needle, comprising distal and proximal portions. The elongate member delivery assembly includes an elongate body defining an axis and a laterally-extending layer-separation guide at the distal end of the body. The guide is sized and shaped to guide the distal end of the delivery assembly between the layers of a tubular body structure. The guide helps to ensure the device stays between the chosen layers so to help prevent inadvertent puncturing or other damage to the wall. The needle delivery assembly further comprises an elongate member-redirecting surface positioned and oriented to cause the tip portion of a distally moving elongate member to be redirected to move in a direction at an angle to the axis. Thus, the tip portion of the elongate member may be directed by the assembly into the wall of a tubular body structure, along the wall between the layers of the wall, past a position (such as an obstruction) in the tubular body structure (such as a blood vessel), and back through at least one of the wall layers to enter the interior of the tubular body structure distally of the position.

The separation guide may have a width of preferably about 2-8 times, and more preferably about 4 times, as wide as the elongate body. The separation guide may have a curved cross-sectional shape. The needle delivery assembly may have a proximal end adapter at the proximal end of the body. The proximal end adapter may have a component for selecting the maximum movement of the elongate member through the lumen of the body in a distal direction. The separation guide may be moveable between a laterally retracted state and a laterally extended state to permit the assembly to be used percutaneously. The elongate body may include a hollow outer sheath, from which the separation guide extends, and an elongate member support element housed within the outer sheath and at least partly defining an elongate member pathway, the elongate member support element comprising the elongate member-redirecting surface.

A second aspect of the invention is directed to a method for crossing a position along a tubular body structure, such as a vascular occlusion, comprising selecting a position-crossing assembly comprising a flexible elongate member and an elongate member delivery assembly. The delivery assembly comprises an elongate body, a laterally-extending separation guide and an elongate member-redirecting surface positioned and oriented to cause the tip portion of a distally moving elongate member to be redirected to move in a direction at an angle to the axis of the body. The method further includes positioning the laterally-extending separation guide between layers of the wall of the tubular body structure; passing the guide between layers from a position proximal of a position within the blood vessel interior to a position distal of the position, typically past an obstruction; and then driving the elongate member along the axis in a distal direction against the deflecting surface thereby deflecting the tip portion causing the tip portion to pass through at least one wall layer and into the interior of the hollow body structure.

The method may include adjusting the maximum distance the elongate member may extend distally past the elongate member-redirecting surface. The method may also include injecting a detectable substance through the elongate member and into a blood vessel interior following the driving step to ensure the tip is properly positioned, typically within the vessel interior distal of an occlusion. The selecting step may further comprise choosing a laterally-extending, vascular tunica-separation guide having a shape which defines a curved tunicae-separation plane, the plane sized to generally follow the curvature of the blood vessel. The positioning step may be carried out percutaneously; the positioning step may comprise changing the state of the tunica-separation guide from a laterally-retracted state to a laterally-extended state to aid percutaneous placement. It should be noted that although the invention has been described in terms of use in permitting a guidewire to cross an occlusion, it could be used when a vessel is not totally occluded or in situation where the vessel is not occluded at all.

Other features and advantages of the invention will appear from the following description in which the preferred embodiments and methods are set forth in detail in conjunction with the accompanying drawings.

BRIEF DESCRIPTION OF THE DRAWINGS

FIG. 10 is a cross-sectional view of the assembly of FIG. 9;

FIG. 10A is a view similar to that of FIG. 10 but with the guidewire support element rotated 180° and the guidewire moved distally and deflected by the deflecting surface on the guidewire support element to pass out an opening in the outer sheath;

FIG. 13 is a perspective view of portions of the handle of FIG. 9.

DESCRIPTION OF THE SPECIFIC EMBODIMENTS

Figure 1:
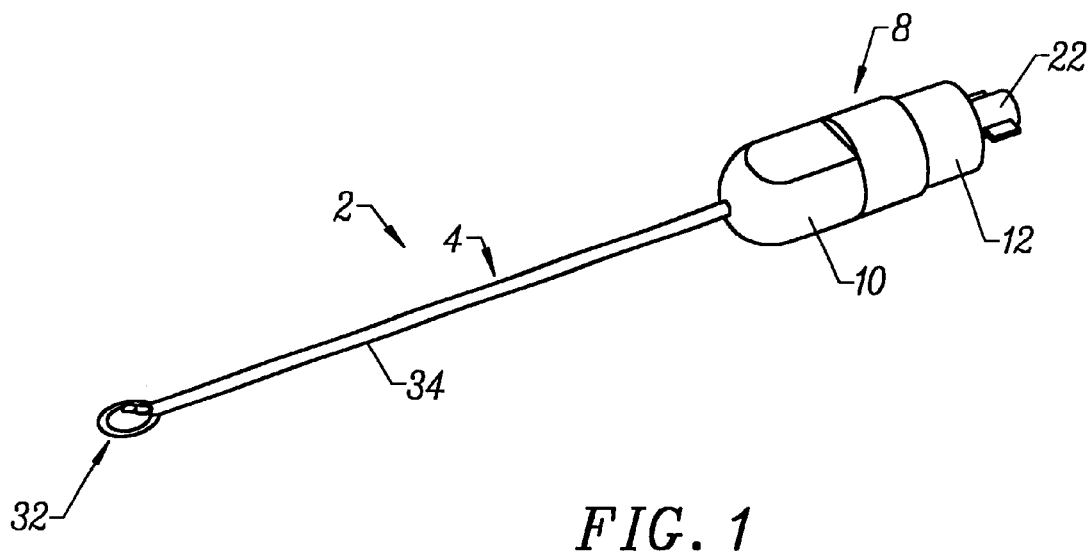
FIG. 1 is an overall view of a vascular occlusion-crossing assembly made according to the invention.
Figure 2:
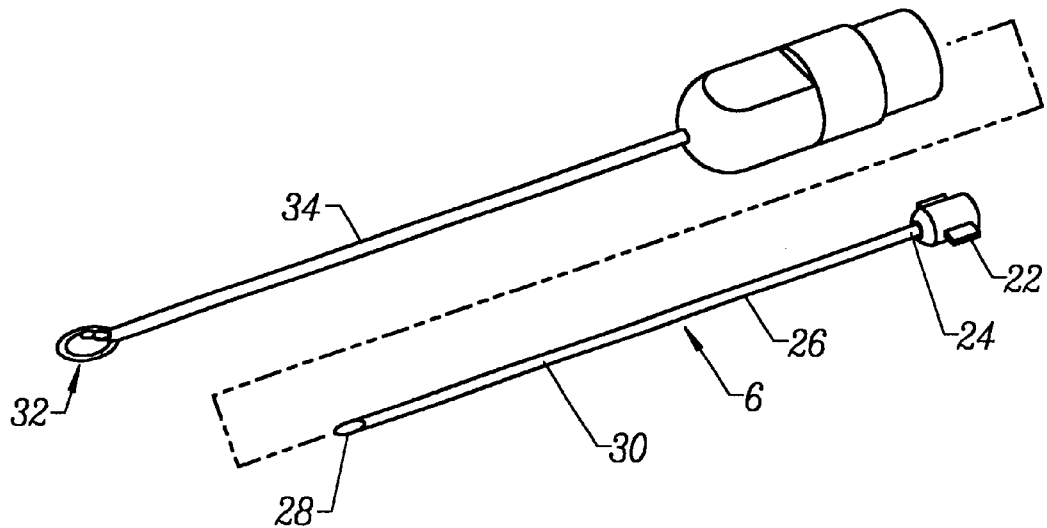
FIG. 2 is an exploded isometric view of the assembly of FIG. 1 in which the hollow needle is shown removed from the needle delivery assembly.

FIGS. 1 and 2 illustrate a vascular occlusion-crossing assembly 2 made according to the invention. Assembly 2 includes a needle delivery assembly 4 which houses a hollow needle 6 or other elongate member.

Figure 3:
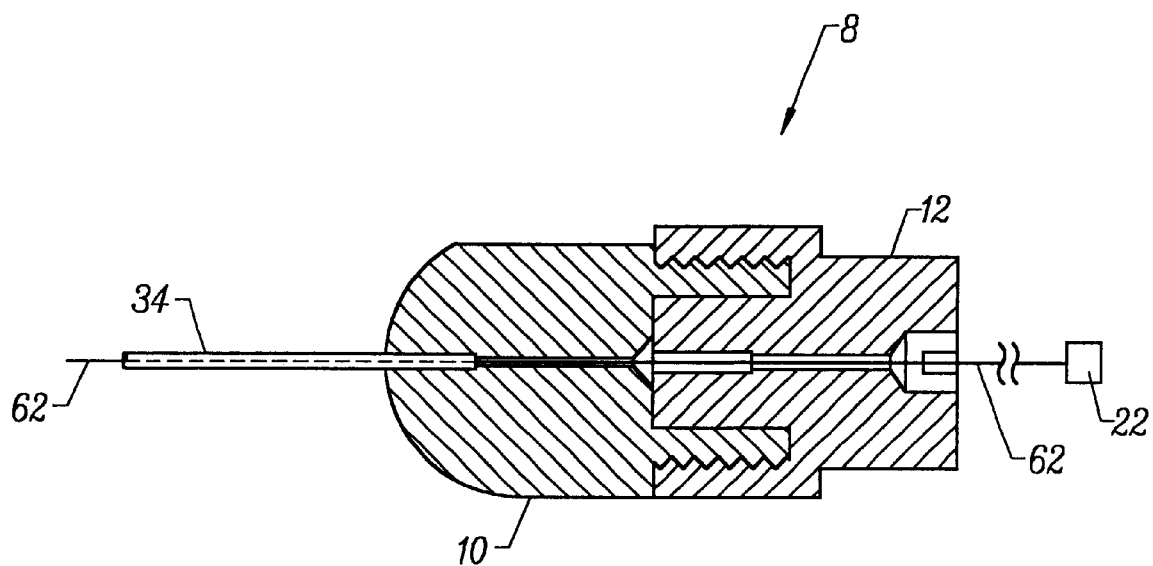
FIG. 3 is a cross-sectional view of the handle of FIG. 1 with a proximal portion of the hollow needle passing therethrough.
Figure 3A:
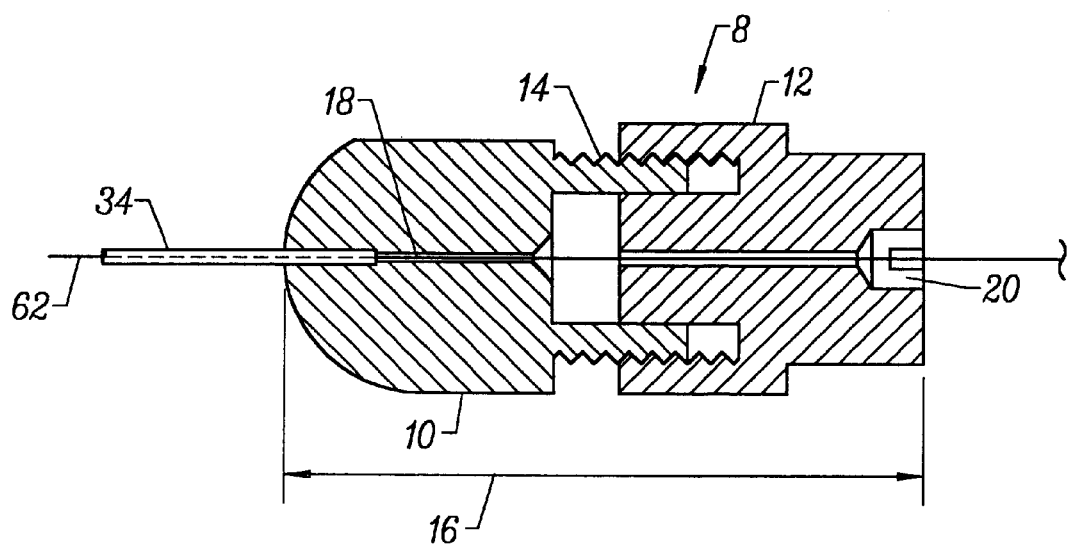
FIG. 3A is a view similar to that of FIG. 3 but with length of the handle increased by rotating the rear handle relative to the front handle.

Needle delivery assembly 4 includes a handle 8, see FIGS. 3 and 3A, as its proximal end adapter. Handle 8 includes a front handle body 10 and a rear handle body 12. Front and rear handle bodies are threadably mounted to one another at threads 14 so that the length 16 of a bore 18 extending through the handle can be adjusted by the user; the purposes of this feature will be discussed in more detail below. Rear handle body 12 has a recess 20 at the proximal end of bore 18 sized to accommodate the Luer fitting 22 at the proximal portion 24 of hollow needle 6. Hollow needle 6 includes a hollow needle shaft 26 extending from Luer fitting 22 to a sharpened tip 28 at a tip portion 30 of needle 6. Needle 6 is hollow to permit both a passage of a guidewire, or other elongate structures, and/or a contrast fluid therethrough, the use of which is discussed below. Hollow needle 6 also permits the flow of blood back through the needle to provide an indication to the user when an artery is located.

Figure 4:
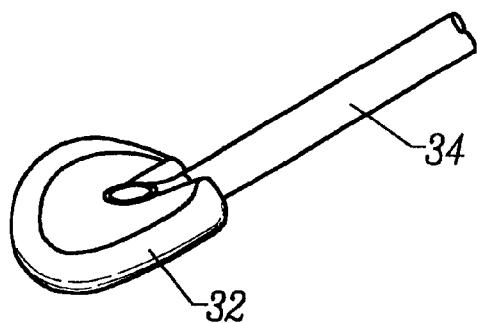
FIG. 4 is an enlarged isometric view of the distal portion of the assembly of FIG. 1.
Figure 5:
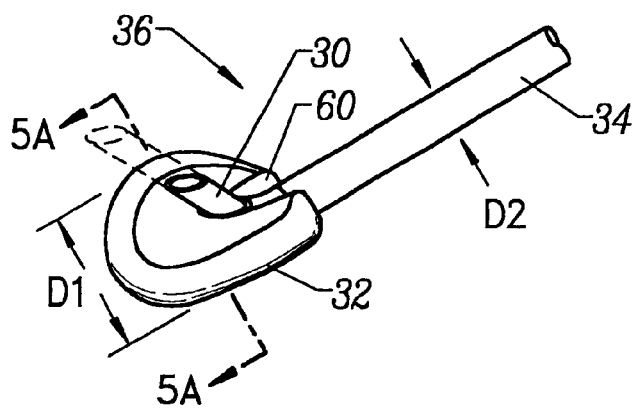
FIG. 5 is a view similar to that of FIG. 4 but sting the tip of the needle passing through the separation guide to view two different extents.
Figure 5A:
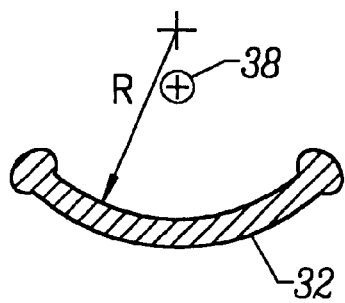
FIG. 5A is a cross-sectional taken along line 5A–5A of FIG. 5 illustrating the curved shape of the separation guide along a plane perpendicular to the axis of the elongate body.
Figure 6:
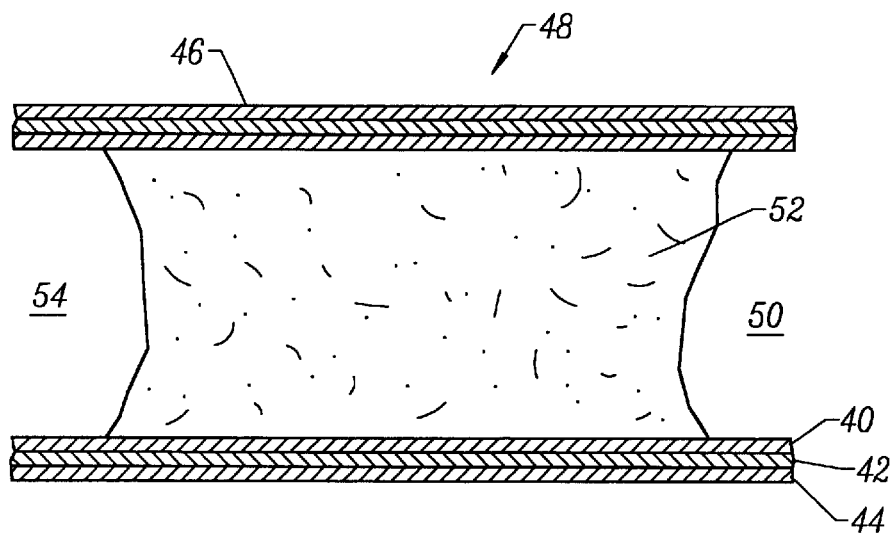
FIG. 6 is a greatly enlarged cross-sectional view of a blood vessel with a total occlusion within the blood vessel interior, the three layers of the blood vessel wall being shown by separate cross hatching.
Figure 7:
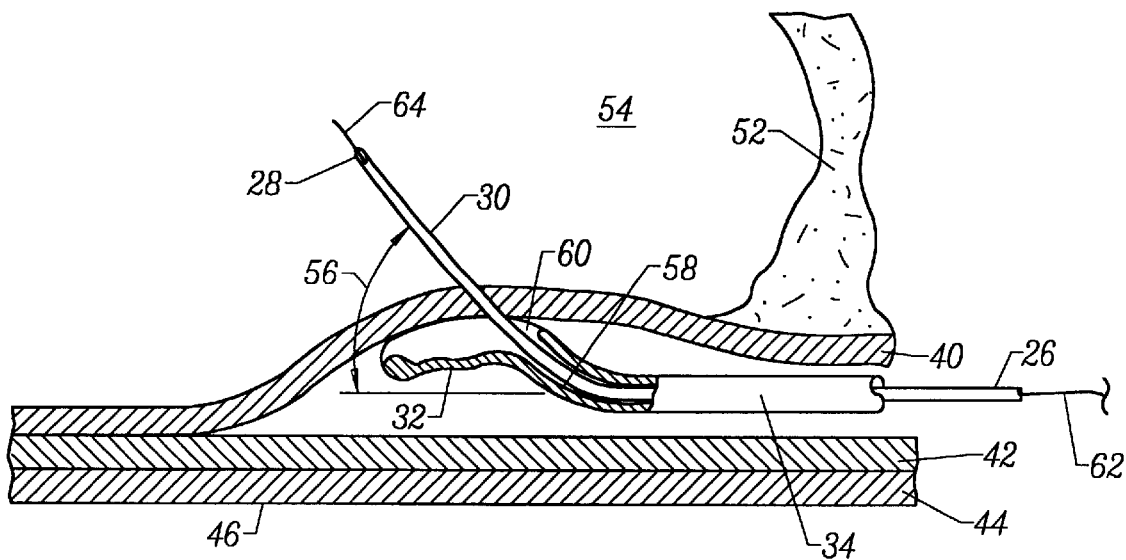
FIG. 7 shows the distal portion of the assembly of FIG. 1 after the needle-redirecting surface has entered the blood vessel wall at an entrance position proximal of the occlusion (shown in FIG. 6), and after passing between the tunica intima and tunica media to position distal of the total occlusion; also shown is the tip of the hollow needle having been redirected by the needle-redirecting surface of the separation guide to pass through the tunica intima and into the distal lumen distal of the occlusion; also shown is a guidewire passing through the hollow needle and into the distal lumen.

FIGS. 4, 5 and 5A illustrate the construction of a vascular tunicae-separation guide 32 extending from a hollow, elongated body 34 at the distal end 36 of assembly 4. Guide 32 is preferably sized and shaped and constructed to generally follow the curvature of the blood vessel with which it is to be used. As shown in FIG. 5A, taken along a plane oriented perpendicular to the axis 38 of the elongate body 34, separation guide 32 has a generally curved shape with an average radius of curvature R of about 3 mm to 15 mm and more preferably about 6 mm to 8 mm for vascular use. Radius R is chosen according to the radius of the vessel or other tubular structure. Also, the maximum width DI of separation guide 32 is preferably about 2 to 8 times, and typically about 4 times, the width D2 of elongate body 34. The curved or circumferential width W of separation guide 32 is measured along an arc and this is longer than straight-line width DI. Circumferential width W is preferably about ¼ to ½ of the circumference of the blood vessel, or other tubular body structure, with which it is to be used. The appropriate sizing and shaping of separation guide 32 helps to ensure that the distal end 32 of needle delivery assembly 4 is properly guided along the dissection plane between two of the three tunicae intima 16, tunica media 42 and tunica adventitia 14, illustrated in FIGS. 6 and 7, of the blood vessel wall 46 of blood vessel 48.

In use, access through blood vessel wall 46 is made to provide access into proximal lumen 50 located proximal of a total occlusion 52 within blood vessel 48. Separation guide 32 is inserted into vessel wall 46 at entrance point 53 within proximal lumen 50 and into a dissection plane, typically between tunica intima 40 and tunica adventitia 44. Separation guide 32 is then advanced to a position distal of the intended core transection point, in this case distal of total occlusion 52, as suggested in FIG. 7. Hollow needle shaft 26 of hollow needle 6 is then passed through hollow body 34 where it is directed into distal lumen 54 at angle 56 to axis 38 by a needle-redirecting surface 58. Surface 58 is formed by the distal end of elongate body 34 as the body curves at an angle to axis 38 so that the tip portion 30 of hollow needle shaft 26 passes out of the opening 60 at the distal end of body 34 adjacent to separation guide 32. Angle 56 is about 0° to 90°, and is preferably about 30° to 60°, and is more preferably about 45°. To ensure tip 28 is at the desired position, in this case within distal lumen 54, contrast media is then flushed under fluoroscopic imaging through Luer fitting 32. This helps to ensure the true lumen, that is, distal lumen 54, has been accessed as opposed to a false lumen within vessel wall 46 or a region external of blood vessel 48.

It is typically desirable to limit the distance tip 28 can extend past opening 60 so to help prevent tip 28 from passing completely through blood vessel 48. To do so, the user typically first inserts hollow needle 6 into delivery assembly 4 until Luer fitting 22 is properly housed within recess 20. This occurs prior to placing assembly 2 within the patient. This indicates the maximum distance tip 28 can extend from opening 60 at distal end 36. See the dashed line position of tip 28 of FIG. 5. The user then rotates front and rear handle bodies 10, 12 relative to one another thus causing the length 16 of bore 18 to increase until tip 28 is at a desired distance from opening 60. See the solid line position of tip 28 of FIG. 5. At this point hollow needle 6 is typically removed from assembly 4 and then separation guide 32 is positioned distally of occlusion 52 as discussed above and shown in FIG. 7. Hollow needle 6 is then reintroduced fully into assembly 4 so that tip 28 is deflected by surface 58, passes through tunica intima 40 and enters distal lumen 54. Once tip 28 has been confirmed to be properly positioned, typically with the aid of a contrast media, a guidewire 62 is passed through hollow needle shaft 26 until the tip 64 of guidewire 62 is positioned within distal lumen 54. Guidewire 62 is then anchored relative to needle delivery assembly 4 to permit hollow needle 6 to be removed from blood vessel 48. The desired result of providing a guidewire crossing total occlusion 52 within blood vessel 48 has now been achieved. At this point the surgeon may proceed with any one of several diagnostic or therapeutic procedures. For example, a section of intimal layer 40 with occlusion 52 therein may be removed by remote endarterectomy; after which guidewire 62 can be used to help place any balloon, stent, lining or other endovascular device into vessel 48.

The materials from which the components of assembly 2 may be made include any of a number of biocompatible materials. For example body 34 and guide 32 may be made of polymers, metals and ceramics, or a combination thereof, such as stainless steel or Nitinol, while handle 8 will typically be made of one or more polymers. Needle shaft 26 is typically made of Nitinol, stainless steel or polymers, or a combination thererof, e.g. a stainless steel body with a Nitinol tip.

Figure 8A:
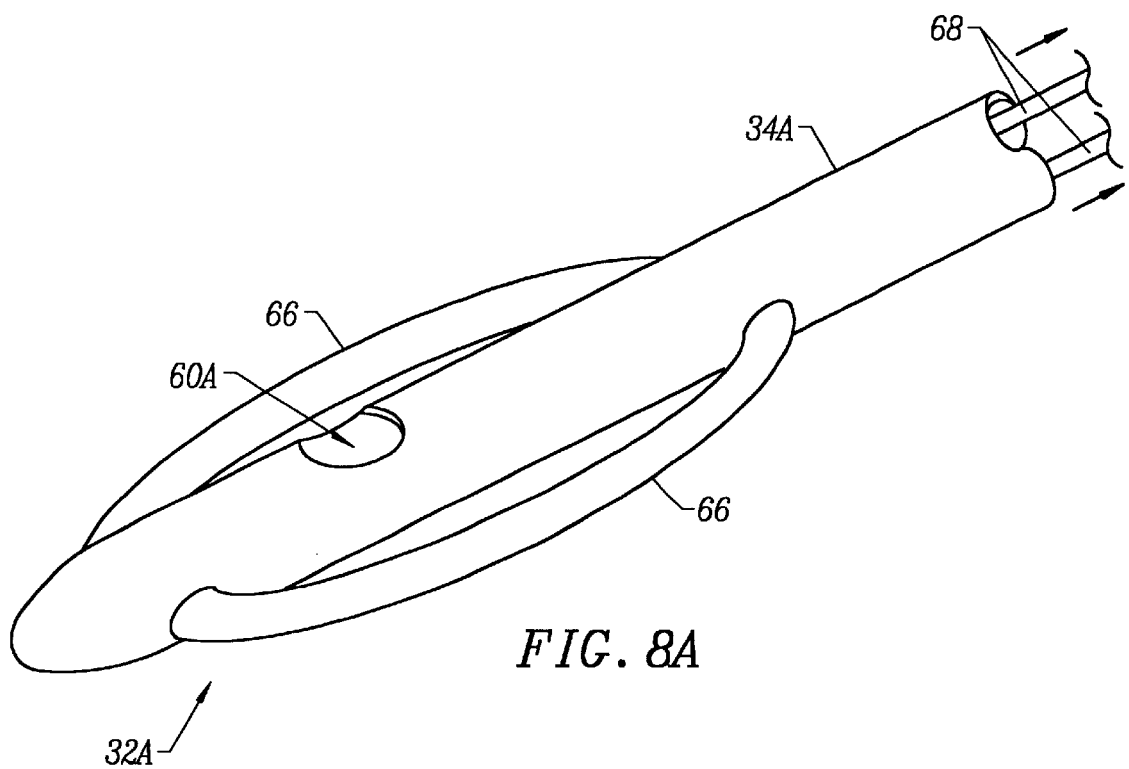
FIGS. 8A and 8B show the distal end of an alternative embodiment of the needle delivery assembly of FIGS. 1 and 4, showing the separation guide in laterally-retracted and laterally-extended states, respectively.
Figure 8B:
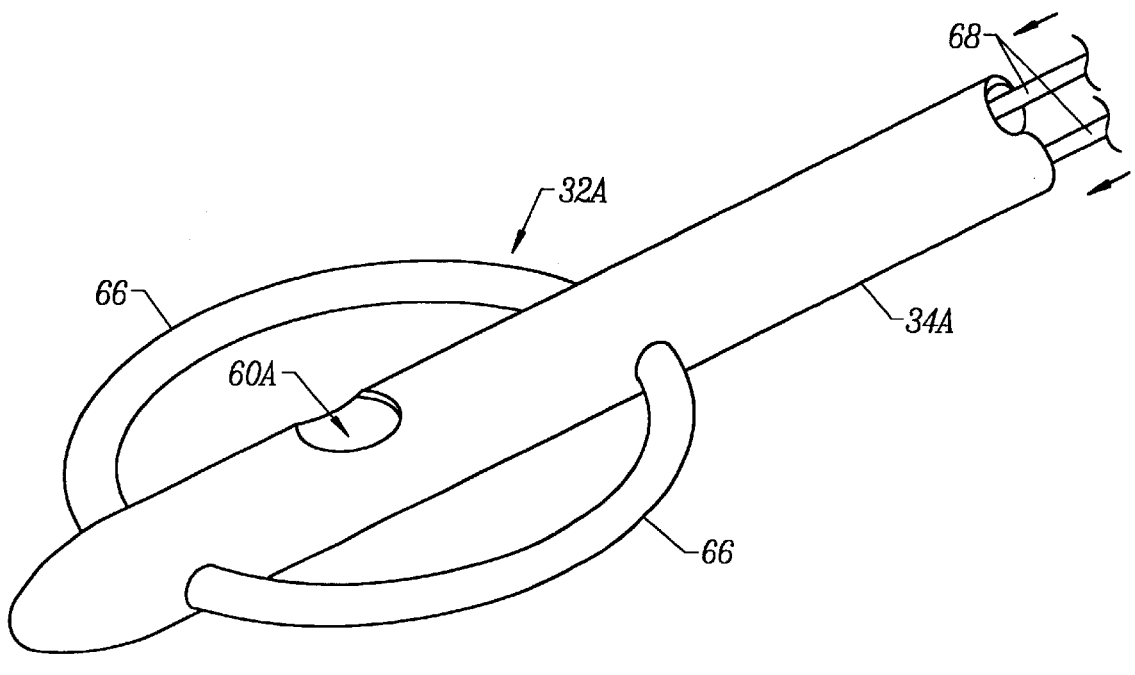
Figure 9:
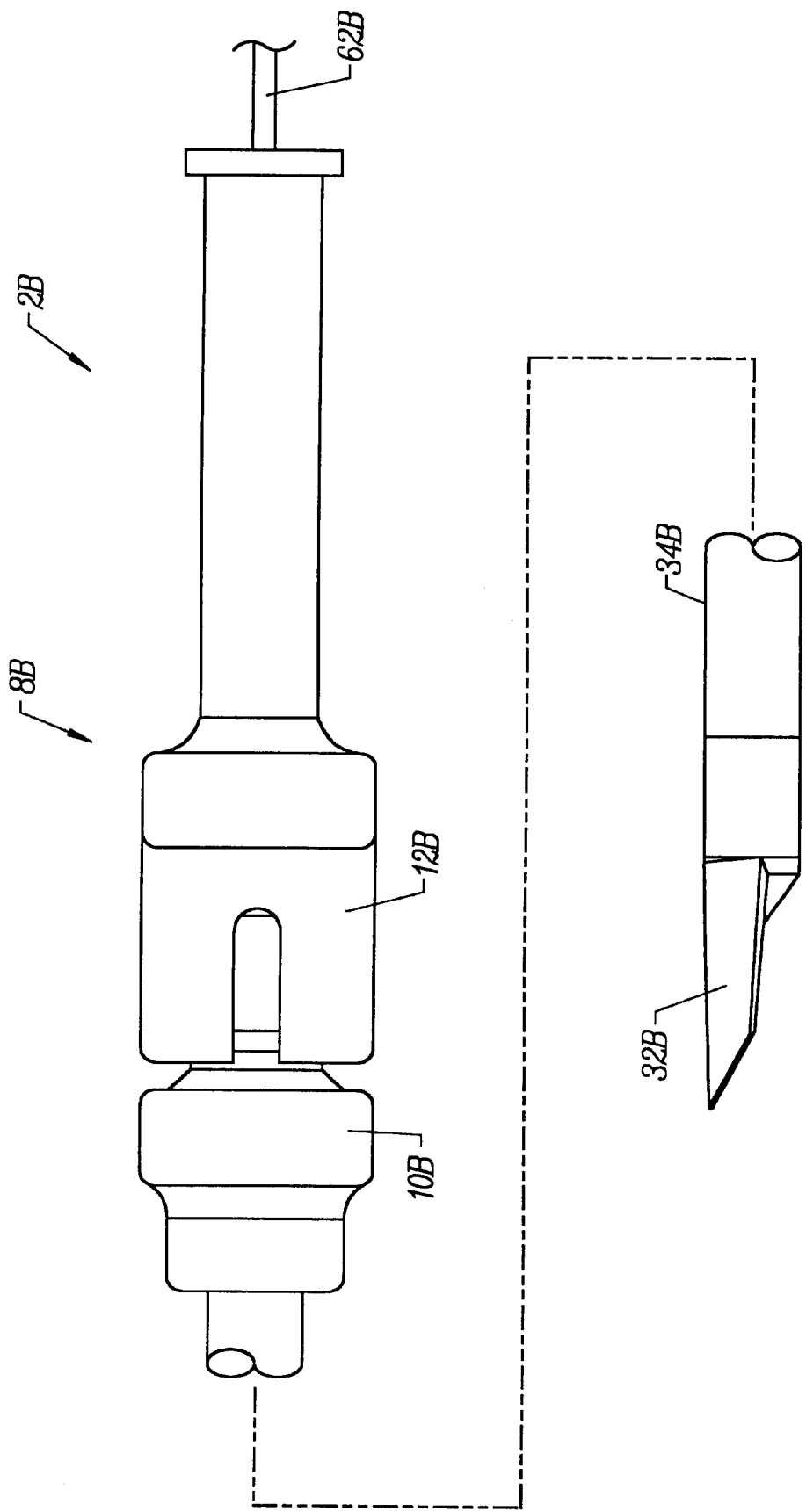
FIG. 9 is an enlarged side view of the proximal and distal ends of an alternative embodiment of the assembly of FIG. 1.
Figure 11:
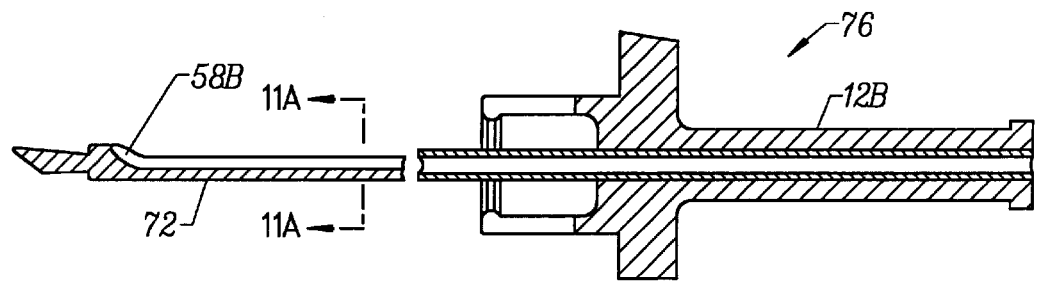
FIG. 11 is a side cross-sectional view of the guidewire support element assembly of FIG. 9 including the guidewire support element of FIG. 10 and the rear handle body of FIG. 9.
Figure 11A:
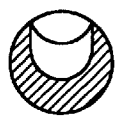

FIGS. 8A and 8B illustrate the distal end of an alternative embodiment of the invention, specially designed for percutaneous use. Vascular tunicae-separation guide 32A can assume a laterally-retracted state shown in FIG. 8A and a laterally-extended state shown in FIG. B. Separation guide 32A includes a pair of laterally outwardly extending, flexible guide members 66 which tend to assume the laterally extended state of FIG. 8B. To assume the laterally-retracted state of FIG. 8A, the user pulls on a pair of pull wires 68 which pull a portion of each guide member 66 back into body 34A of the needle delivery assembly for percutaneous introduction into proximal lumen 50 of blood vessel 48. Alternatively, guide member 66 could be made of a shape memory material which would assume a laterally-extended state of FIG. 8B either by virtue of being heated to, for example, body temperature or in some other manner. It is preferred that guide member 66 be sufficiently flexible so to permit them to generally follow the natural dissection plane between the tunica layers of the blood vessel. It should be noted that the straight-line and circumferential widths of guide 32A corresponding to widths D1 and W of the embodiment of FIGS. 5 and 5A are the same when guide 32A is in the FIG. 8B state. One or more fluoroscopically visible, or other remotely visible, markers are preferably used on guide 32A to help ensure proper orientation of the guide within the patient so that the needle is properly directed into the vessel lumen.

Figure 12:
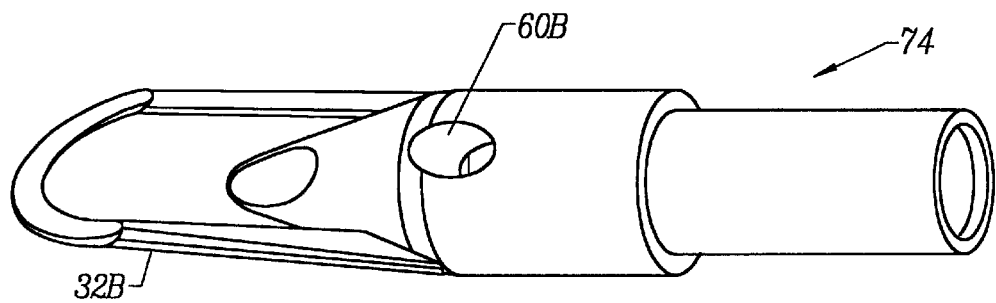
FIG. 12 is an isometric view of a tip element of the needle delivery assembly of FIG. 9 separated from the hollow outer sheath and with the guidewire support element and guidewire removed.
Figure 12A:
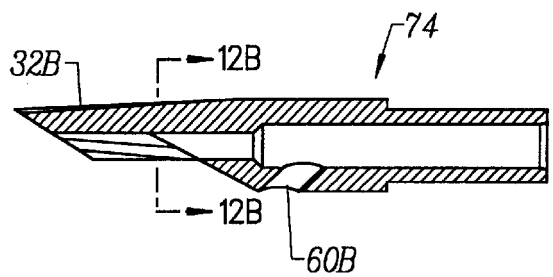
FIG. 12A is a longitudinal cross-sectional view of the tip element of FIG. 12.
Figure 12B:
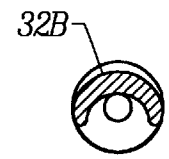
FIG. 12B is a cross-sectional view taken along line 12B–12B of FIG. 12A.

A further embodiment of the invention is disclosed in FIGS. 9–13. In this embodiment elongated body 34B includes both a hollow outer sheath 70, extending from front handle body 10B, and a elongated guidewire support element 72, housed within sheath 70. See FIG. 11. Guidewire support element 72 is secured to and extends from rear handle body 12B. Vascular tunica-separation guide 32B, shown best in FIGS. 12, 12A and 12B, is made as part of a tip element 74 secured to and extending from hollow outer sheath 70. Guidewire support element 72 and rear handle body 12 together constitute guidewire support element assembly 76. Assembly 76 is typically oriented in one of two rotary orientations, 180° apart, as shown in FIGS. 10 and 10A. The orientation of FIG. 10 is used when assembly 2B is being passed between tunica intima 40 and tunica media 42 or between tunica media 42 and tunica adventitia 44. This orientation helps to create a smooth tissue deflecting surface 78, shown in FIG. 10, during this procedure. Once properly in position, rear handle body 12 is pulled proximally so pins 80, extending from front handle body 10B, become disengaged from slots 82 formed in rear handle body 12B; rear handle body 12B is then rotated 180O and then moved distally to seat pin 80 within the opposite slot 84. At this position, needle re-deflecting surface 58B has become oriented with opening 60B so to permit guidewire 62B, or other flexible elongate member, to pass through opening 60B and enter distal lumen 54.

Corresponding elements of the various embodiments have been referred to with reference numerals so they are not separately described. The common methods of use of the embodiment have also not been separately discussed.

Other modifications can be made through the disclosed embodiment without departing from the subject of the invention as defined in the following claims.

Any and all patents, patent applications and printed publications referred to above are incorporated by reference.

What is claimed is:

1. An assembly for use with a tubular body structure of the type having a wall with layers, comprising:
   an elongate member delivery assembly comprising:
      an elongate body having proximal and distal ends and defining an axis; and
      a laterally-extending, layer-separation guide at the distal end, the guide sized and shaped to guide the distal end of the delivery assembly between layers of a wall of a tubular body structure;
   a flexible elongate member comprising a proximal portion and a distal portion passable along the elongate body, the distal portion comprising a tip; and
   the assembly further comprising a elongate member-redirecting surface positioned and oriented to cause the distal portion of a distally moving elongate member to be redirected to move in a direction at an angle to the axis;
   whereby the distal portion may be directed by the assembly into a wall of the tubular body structure, along the tubular body structure between layers of the wall of the tubular body structure, past a position in the tubular body structure, and back through at least one of the layers to enter the tubular body structure distally of the position.

2. The assembly according to claim 1 wherein the layer-separation guide comprises a vascular tunica-separation guide for placement between tunicae of a blood vessel.

3. The assembly according to claim 1 wherein the elongate body defines a lumen through which the elongate member passes.

4. The assembly according to claim 3 wherein the elongate member delivery assembly comprises a proximal end adapter at the proximal end of the body, and wherein the proximal end adapter comprises means for selecting the maximum movement of the elongate member through the lumen of the elongate body in a distal direction.

5. The assembly according to claim 1 wherein the separation guide has a width about 2–8 times as wide as the elongate body.

6. The assembly according to claim 1 wherein the separation guide has a width about 4 times as wide as the elongate body.

7. The assembly according to claim 1 wherein the separation guide defines an imperforate surface.

8. The assembly according to claim 1 wherein the separation guide defines a surface having an opening formed therein.

9. The assembly according to claim 1 wherein the separation guide has a curved cross-sectional shape along a plane oriented perpendicular to the axis.

10. The assembly according to claim 1 wherein the separation guide defines a curved tunicae-separation plane surface.

11. The assembly according to claim 10 wherein said plane has an average radius of curvature of between about 3 mm and 15 mm.

12. The assembly according to claim 1 wherein the elongate member comprises a hollow needle and an injectable-material entrance port.

13. The assembly according to claim 12 wherein said injectable-material entrance port comprises a fitting.

14. The assembly according to claim 1 wherein the elongate member comprises a hollow needle, and further comprising a guidewire directable through the hollow needle.

15. The assembly according to claim 1 wherein said elongate member-redirecting surface is located at the separation guide.

16. The assembly according to claim 1 wherein at least a portion of the elongate member-redirecting surface is a curved surface.

17. The assembly according to claim 1 wherein the elongate member-redirecting surface is configured to cause the angle to be about 30° to 60°.

18. The assembly according to claim 1 wherein the elongate member delivery assembly comprises a proximal end adapter at the proximal end of the body.

19. The assembly according to claim 18 wherein the proximal end adapter comprises means for adjustably limiting the distance the elongate member can move distally relative to the elongate body.

20. The assembly according to claim 18 wherein the elongate member comprises an elongate member stop element at a proximal portion thereof.

21. The assembly according to claim 20 wherein:
   the proximal end adapter comprises a front handle to which a rear handle is movably mounted, the front and rear handles defining a through hole through which the elongate member passes;
   a chosen one of the front and rear handles comprising a stop surface engagable by the elongate member stop element; and
   the effective length of the through hole being adjustable by a user adjusting the position of at least one of the front and rear handles relative to the other.

22. The assembly according to claim 21 wherein the rear handle is threadably mounted to the front handle.

23. The assembly according to claim 20 wherein the proximal end adapter comprises a user-positionable stop surface engagable by a user so to permit a user to limit the distal movement of the elongate member.

24. The assembly according to claim 1 wherein the layer-separation guide is movable between a laterally-retracted state and a laterally-extended state to permit the assembly to be used percutaneously.

25. The assembly according to claim 24 wherein the layer-separation guide is biased towards said laterally-extended state.

26. The assembly according to claim 25 further comprising means for moving the layer-separation guide from the laterally-extended state to the laterally-retracted state.

27. The assembly according to claim 1 wherein the elongate member comprises a hollow needle and said tip comprises a sharpened tip.

28. An assembly for use with a tubular body structure of the type having a wall with layers, comprising:
- an elongate member delivery assembly comprising:
  - an elongate body having proximal and distal ends and defining an axis; and
  - a laterally-extending, layer-separation guide at the distal end, the guide sized and shaped to guide the distal end of the delivery assembly between layers of a wall of a tubular body structure;
- a flexible elongate member comprising a proximal portion and a distal portion passable along the elongate body, the distal portion comprising a tip;
- the assembly further comprising a elongate member-redirecting surface positioned and oriented to cause the distal portion of a distally moving elongate member to be redirected to move in a direction at an angle to the axis;
- the elongate body comprising a hollow outer sheath, from which the guide extends, and an elongate member support element housed within the outer sheath and at least partly defining an elongate member pathway, said elongate member support element comprising said elongate member-redirecting surface; and
- whereby the distal portion may be directed by the assembly into a wall of the tubular body structure, along the tubular body structure between layers of the wall of the tubular body structure, past a position in the tubular body structure, and back through at least one of the layers to enter the tubular body structure distally of the position.

29. The assembly according to claim 28 wherein said guide has a semicircular cross-sectional shape.

30. The assembly according to claim 28 wherein said hollow sheath comprises an exit lumen at the proximal end of the elongate body.

31. The assembly according to claim 30 wherein said elongate member support element is rotatable within the outer sheath so to position the elongate member-redirecting surface aligned with and offset from the exit lumen.

32. The assembly according to claim 28 wherein the elongate member support element is rotatable within the outer sheath for movement between first and second rotary orientations.

33. The assembly according to claim 32 wherein the guide comprises a curved distal edge and a tapered tissue-cleaving surface having a central opening therein, said elongate member support element comprising a tissue-cleaving surface portion alignable with the central opening when the elongate member support element is at the first rotary orientation.

34. An assembly for use with a tubular body structure of the type having a wall with layers, comprising:
- an elongate member delivery assembly comprising:
  - an elongate body having proximal and distal ends and defining an axis; and
  - a laterally-extending, layer-separation guide at the distal end, the guide sized and shaped to guide the distal end of the delivery assembly between layers of a wall of a tubular body structure; and
- a flexible elongate tube comprising a proximal portion and a distal portion passable along the elongate body, the distal portion comprising a tip, the proximal portion comprising an injectable-material entrance port;
- whereby the distal portion may be directed by the assembly into a wall of the tubular body structure, along the tubular body structure between layers of the wall of the tubular body structure, past a position in the tubular body structure, and back through at least one of the layers to enter the tubular body structure distally of the position, whereby a remotely sensable material may be injected through the tube and into blood vessel to permit remote confirmation of proper placement of the tube.

35. The assembly according to claim 34 wherein the tube is a hollow needle and the injectable material entrance port comprises a fluid fitting.

36. The assembly according to claim 34 further comprising a guidewire directable through the tube.

37. A vascular occlusion-crossing assembly comprising:
- an elongate member delivery assembly comprising:
  - an elongate body having proximal and distal ends and defining an axis;
  - a proximal end adapter at the proximal end;
  - a laterally-extending, vascular tunica-separation guide at the distal end, the guide sized and shaped to guide the distal end of the delivery assembly between tunicae of a blood vessel;
- a flexible elongate member comprising:
  - a hollow needle comprising proximal and distal portions;
  - an injectable-fluid entrance-port at the proximal portion; and
  - the tip portion passable along the elongate body, the tip portion comprising a tip;
- the assembly further comprising a elongate member-redirecting surface positioned and oriented to cause the tip portion of a distally moving elongate member to be redirected to move in a direction at an angle to the axis;
- a guidewire directable through the hollow needle;
- the proximal end adapter comprising means for selecting the maximum movement of the elongate member through the lumen of the elongate body in a distal direction;
- whereby the distal portion may be directed by the assembly into a blood vessel wall, along blood vessel between tunicae of the blood vessel, past an obstruction in the blood vessel and back through at least one of the blood vessel tunicae to enter the blood vessel distally of the obstruction, after which a remotely sensable material may be injected through the hollow needle and into the blood vessel to permit remote confirmation of proper placement of the hollow needle, after which the guidewire may be placeable through the hollow needle, and after which one or both of the delivery assembly and elongate member may be removed leaving the guidewire in place.

38. The assembly according to claim 37 wherein the separation guide has a width about 2 to 8 times as wide as the elongate body.

39. The assembly according to claim 37 wherein the separation guide defines a curved tunicae-separation surface.

40. The assembly according to claim 37 wherein the tunica-separation guide is movable between a laterally-retracted state and a laterally-extended state to permit the assembly to be used percutaneously.

41. A vascular occlusion-crossing assembly of the type comprising a flexible elongate member, having a tip portion, and an elongate member delivery system comprising an elongate body, along which the elongate member passes, and a redirecting surface positioned and oriented to cause the distal portion of a distally moving elongate member to be redirected to move in a direction at an angle to the axis, whereby the tip portion may be directed by the assembly into a blood vessel wall, along the blood vessel between tunicae of the blood vessel, past an obstruction in the blood vessel and back through at least one of the blood vessel tunicae to enter the blood vessel distally of the obstruction, the improvement comprising:

a laterally-extending, partially circumferentially-extending, vascular tunica-separation guide at the distal end, the guide sized and shaped to guide the distal end of the delivery assembly between tunicae of a blood vessel.

42. A vascular occlusion-crossing assembly the type comprising a flexible elongate member, having a tip portion, and an elongate member delivery system comprising an elongate body, along which the elongate member passes, and a redirecting surface positioned and oriented to cause the distal portion of a distally moving elongate member to be redirected to move in a direction at an angle to the axis, whereby the tip portion may be directed by the assembly into a blood vessel wall, along the blood vessel between tunicae of the blood vessel, past an obstruction in the blood vessel and back through at least one of the blood vessel tunicae to enter the blood vessel distally of the obstruction, the improvement comprising:

the elongate member comprising a tube with a flowable material entrance port at a proximal end thereof, so that a remotely sensable material may be injected through the tube and into the blood vessel to permit remote confirmation of proper placement of the tube.

43. The assembly according to claim 42 further comprising a guidewire placeable through the tube so one or both of the elongate member delivery system and the elongate member may be removed from a patient leaving the guidewire in place.

44. A method for crossing a position along a tubular body structure comprising:

selecting a position-crossing assembly comprising:
a flexible elongate member;
an elongate member delivery assembly comprising an elongate body, having proximal and distal ends and defining an axis, a laterally-extending separation guide at the distal end, the guide sized and shaped to guide the distal end of the delivery assembly between layers of a wall of a tubular body structure, and an elongate member-redirecting surface positioned and oriented to cause the distal portion of a distally moving elongate member to be redirected to move in a direction at an angle to the axis;

positioning the laterally-extending separation guide between wall layers of a tubular body structure;

passing the guide between the wall layers from a location proximal of a position along the tubular body structure to location distal of the position; and then driving the elongate member along the axis distal direction against the deflecting surface thereby deflecting the tip portion causing the distal portion to pass through at least one wall layer and into the interior of the tubular body structure.

45. The method according to claim 44 wherein the guide passing step is carried out between a tunica intima and a tunica media of a blood vessel.

46. The method according to claim 45 wherein the selecting step further comprises selecting a separation guide having a circumferential width of between about ¼ to ½ of the circumference of a blood vessel with which the assembly is to be used.

47. The method according to claim 44 wherein the selecting step further comprises selecting a separation guide having a width about 2 to 8 times as wide as the elongate body.

48. The method according to claim 44 further comprising adjusting the maximum distance the elongate member may extend distally past the elongate member-redirecting surface.

49. The method according to claim 48 wherein the adjusting step is carried out prior to the positioning step.

50. The method according to claim 44 further comprising positioning the tip of the elongate member proximal of the elongate member-redirecting surface prior to the positioning step.

51. The method according to claim 44 wherein the passing step is carried out while remotely visualizing the elongate member delivery assembly.

52. The method according to claim 45 further comprising injecting a detectable substance through the elongate member and into a blood vessel interior following the driving step to ensure the tip is properly positioned.

53. The method according to claim 52 wherein the injecting step is carried out by connecting a syringe, containing a remotely visualizable contrast media, to a proximal end of the elongate member.

54. The method according to claim 44 wherein the selecting step is carried out using a flexible, hollow tube as the elongate member.

55. The method according to claim 54 further comprising directing a flexible elongate element through the hollow tube from the proximal end and out through the tip so that the distal end of the elongate element is within the interior of the tubular body structure distally of an occlusion therein.

56. The method according to claim 55 further comprising removing the tube from the patient following the elongate element directing step while maintaining the distal end of the elongate element within said interior.

57. The method according to claim 55 further comprising removing both the tube and the elongate member delivery assembly from the patient following the elongate element directing step while maintaining the distal end of the elongate element within said interior.

58. The method according to claim 55 wherein the directing step is carried out using a flexible guidewire as the elongate element.

59. The method according to claim 45 wherein the selecting step further comprises choosing a laterally-extending, vascular tunica-separation guide having a shape which defines a curved tunicae-separation plane, said plane sized to generally follow the curvature of a blood vessel.

60. The method according to claim 44 wherein the positioning step is carried out percutaneously.

61. The method according to claim 60 wherein the positioning step further comprises changing the state of the tunica-separation guide from a laterally-retracted state to a laterally-extended state.

62. The method according to claim 44 wherein the selecting step comprises selecting an elongate body comprising a hollow outer sheath, from which the guide extends, and an elongate member support element housed within the outer sheath and at least partly defining an elongate member pathway, said elongate member support element comprising said elongate member-redirecting surface.

63. The method according to claim 62 further comprising rotating the elongate member support element within the hollow sheath, following the passing step, thereby positioning the elongate member-redirecting surface to be aligned with an exit lumen formed in a distal end of the sheath.

64. A method for crossing a position along a tubular body structure comprising:

selecting a position-crossing assembly comprising:
- a flexible elongate tube having a tip;
- an elongate member delivery assembly comprising an elongate body, having proximal and distal ends and defining an axis, and a laterally-extending separation guide at the distal end, the guide sized and shaped to guide the distal end of the delivery assembly between layers of a wall of a tubular body structure;

positioning the laterally-extending separation guide between wall layers of a tubular body structure;

passing the guide between the wall layers from a location proximal of a position along the tubular body structure to location distal of the position;

driving the elongate member along the axis in a distal direction causing the distal portion to pass through at least one wall layer and into the interior of the tubular body structure; and injecting a detectable substance through the elongate tube and into the interior of the tubular body structure following the driving step to ensure the tip is properly positioned.

65. The method according to claim 64 further comprising directing a guidewire through the tube after the injecting step.

66. A method for crossing a vascular occlusion comprising:

selecting a vascular occlusion-crossing assembly comprising:
- a flexible elongate member;
- an elongate member delivery assembly comprising an elongate body, having proximal and distal ends and defining an axis, a laterally-extending, vascular tunica-separation guide at the distal end, the guide sized and shaped to guide the distal end of the delivery assembly between tunicae of a blood vessel, and an elongate member-redirecting surface positioned and oriented to cause the tip portion of a distally moving elongate member to be redirected to move in a direction at an angle to the axis;

adjusting the maximum distance the elongate member may extend distally past the elongate member-redirecting surface;

positioning the laterally-extending, vascular tunica-separation guide between blood vessel tunicae;

passing the guide between the tunicae from a position proximal of an obstruction within the blood vessel interior to position distal of the obstruction; and then driving the elongate member along the axis in a distal direction against the deflecting surface thereby deflecting the distal portion causing the tip portion to pass through at least one blood vessel tunicae and into the blood vessel interior;

injecting a detectable substance through the elongate member and into the blood vessel interior following the driving step to ensure the tip is properly positioned;

passing a guidewire through the elongate member following the injecting step; and removing the occlusion-crossing assembly leaving the guidewire in place.

67. The method according to claim 66 wherein the selecting step further comprises choosing a laterally-extending, vascular tunica-separation guide having a shape which defines a curved tunicae-separation plane, said plane sized to generally follow the curvature of the blood vessel.

68. The method according to claim 66 wherein the positioning step is carried out percutaneously.

* * * * *